(12) United States Patent
Skitzki (10) Patent No.: US 12,133,713 B2
(45) Date of Patent: Nov. 5, 2024

(54) CLINICAL INTRAVITAL MICROSCOPE

(71) Applicant: Health Research, Inc., Buffalo, NY (US)

(72) Inventor: Joseph Skitzki, Buffalo, NY (US)

(73) Assignee: Health Research, Inc., Buffalo, NY (US)

( * ) Notice: Subject to any disclaimer, the term of this patent is extended or adjusted under 35 U.S.C. 154(b) by 699 days.

(21) Appl. No.: 16/882,602

(22) Filed: May 25, 2020

(65) Prior Publication Data

US 2020/0281473 A1    Sep. 10, 2020

Related U.S. Application Data

(63) Continuation of application No. 15/307,923, filed as application No. PCT/US2015/029242 on May 5, 2015, now abandoned.

(Continued)

(51) Int. Cl.
*A61B 5/00* (2006.01)
*A61B 5/02* (2006.01)
*A61B 5/026* (2006.01)
*G02B 7/00* (2021.01)
*G02B 21/00* (2006.01)
*G02B 21/02* (2006.01)

(Continued)

(52) U.S. Cl.
CPC ......... *A61B 5/0071* (2013.01); *A61B 5/0077* (2013.01); *A61B 5/02007* (2013.01); *A61B 5/0261* (2013.01); *G02B 7/001* (2013.01); *G02B 21/0012* (2013.01); *G02B 21/0076* (2013.01); *G02B 21/025* (2013.01); *G02B 21/365* (2013.01); *H04N 5/91* (2013.01); *H04N 7/183* (2013.01); *A61B 5/02042* (2013.01); *A61B 2505/05* (2013.01); *A61B 2560/0437* (2013.01)

(58) Field of Classification Search
CPC . A61B 5/0071; A61B 5/0077; A61B 5/02007; A61B 5/0261; G02B 7/001; G02B 21/0012; G02B 21/0076; G02B 21/025; G02B 21/365; H04N 5/91; H04N 7/183
See application file for complete search history.

(56) References Cited

U.S. PATENT DOCUMENTS

2005/0161176 A1\*  7/2005  Brenner ................. A61B 46/10
                                                           160/348
2006/0050376 A1\*  3/2006  Houston ................. G02B 21/16
                                                           359/392

(Continued)

OTHER PUBLICATIONS

Lipponen P, Ji H, Aaltomaa S, Syrjänen K. Tumour vascularity and basement membrane structure in breast cancer as related to tumour histology and prognosis. Journal of cancer research and clinical oncology. Nov. 1994;120(11):645-50. (Year: 1994).\*

*Primary Examiner* — Clifford Hilaire
(74) *Attorney, Agent, or Firm* — Phillips Lytle LLP; David L. Principe (57) ABSTRACT

A clinical intravital microscope with a heavy base; a motorized, mechanized or manual cantilever arm; and a microscope and camera portion at the distal end of the cantilever arm is provided. A method for observing and/or recording conditions such as blood flow, vessel characteristics, such as vessel density, tumor structure, tumor size and dimensions, is provided such that a physician is permitted to observe such information and characteristics in real-time.

17 Claims, 9 Drawing Sheets

Related U.S. Application Data (60) Provisional application No. 61/988,626, filed on May 5, 2014.

(51) Int. Cl.
*G02B 21/36* (2006.01)
*H04N 5/91* (2006.01)
*H04N 7/18* (2006.01)

(56) References Cited

U.S. PATENT DOCUMENTS

| | | | | |
|---|---|---|---|---|
| 2011/0174563 A1* | 7/2011 | Riesner | ............ | B25J 5/007 180/117 |
| 2015/0018622 A1* | 1/2015 | Tesar | ............ | A61B 90/20 600/202 |
| 2016/0202261 A1* | 7/2016 | Pitari | ............ | G01N 33/57484 424/85.4 |

* cited by examiner

CLINICAL INTRAVITAL MICROSCOPE

CROSS-REFERENCE TO RELATED APPLICATION

The present application is a continuation of U.S. patent application Ser. No. 15/307,923 filed Oct. 31, 2016, which is a 371 of International Application No. PCT US/2015/029242 filed May 5, 2015, which claims priority benefit from U.S. Provisional Patent Application No. 61/988,626 filed May 5, 2014, entitled "Clinical Intravital Microscope" which all are incorporated herein by reference.

BACKGROUND OF THE INVENTION

Intravital microscopy ("IVM") is a tool used in preclinical animal experiments to microscopically observe tissue in real time. Intravital microscopy may be applied to the study of cancer. Tumors grown in animals may be observed using intravital microscopy to determine such things as blood vessel characteristics, blood flow features, tumor structure, immune cell and tumor interactions, and drug delivery.

Intravital microscopy offers researchers and others a method of measuring dynamic interactions that are not possible with simple snapshots over time. Microscopic features of human tumors may be measured with simple snapshots in time. Tumors are usually either biopsied or removed, and pathologic evaluation includes fixing the specimen and then performing either stains or other types of analysis that cannot measure dynamic features.

BRIEF SUMMARY OF THE INVENTION

With reference to the corresponding parts, portions or surfaces of the disclosed embodiment, merely for the purposes of illustration and not by way of limitation, one embodiment of the present invention provides an intravital microscope (10) for human use during, among other things, surgical removal of tumors. In one embodiment, the clinical intravital microscope comprises a heavy base or stand (20, 21), a motorized, mechanized or manual cantilever arm (27), and a microscope (31, 36) and camera portion (35) at the distal end of the cantilever arm (27). In one aspect of the invention, a method for observing and/or recording conditions such as blood flow, vessel characteristics, vessel density, tumor structure, tumor size and dimensions, is provided. In another aspect, a physician is permitted to observe such information and characteristics in real-time.

DETAILED DESCRIPTION OF THE PREFERRED EMBODIMENTS

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

During the course of standard surgery to remove a cancerous tumor, while a patient is under anesthesia, access to the tumor tissue is performed surgically either by raising a skin flap or accessing the cavity in which the tumor is growing (e.g. thorax, abdomen, pelvis, etc.). This method may be used in the laboratory to interrogate tumor vasculature in the mouse without the need for window chambers. In one embodiment, pigmentation of the tumor (especially melanoma) does not interfere with the intravital microscopy observation even in densely pigmented lesions. If a skin flap is raised, it will be encompassed by the completion of the wide local excision and will not change the extent of the excision. In another aspect of the invention, the microscope is moved into position next to the operating room table and the wheels locked in place. The microscope may be covered with sterile drape typically used for fluoroscopic C-arms. The only exposed area will be the microscopic objective which is sterile and will be placed at the time of surgery.

Figure 1:
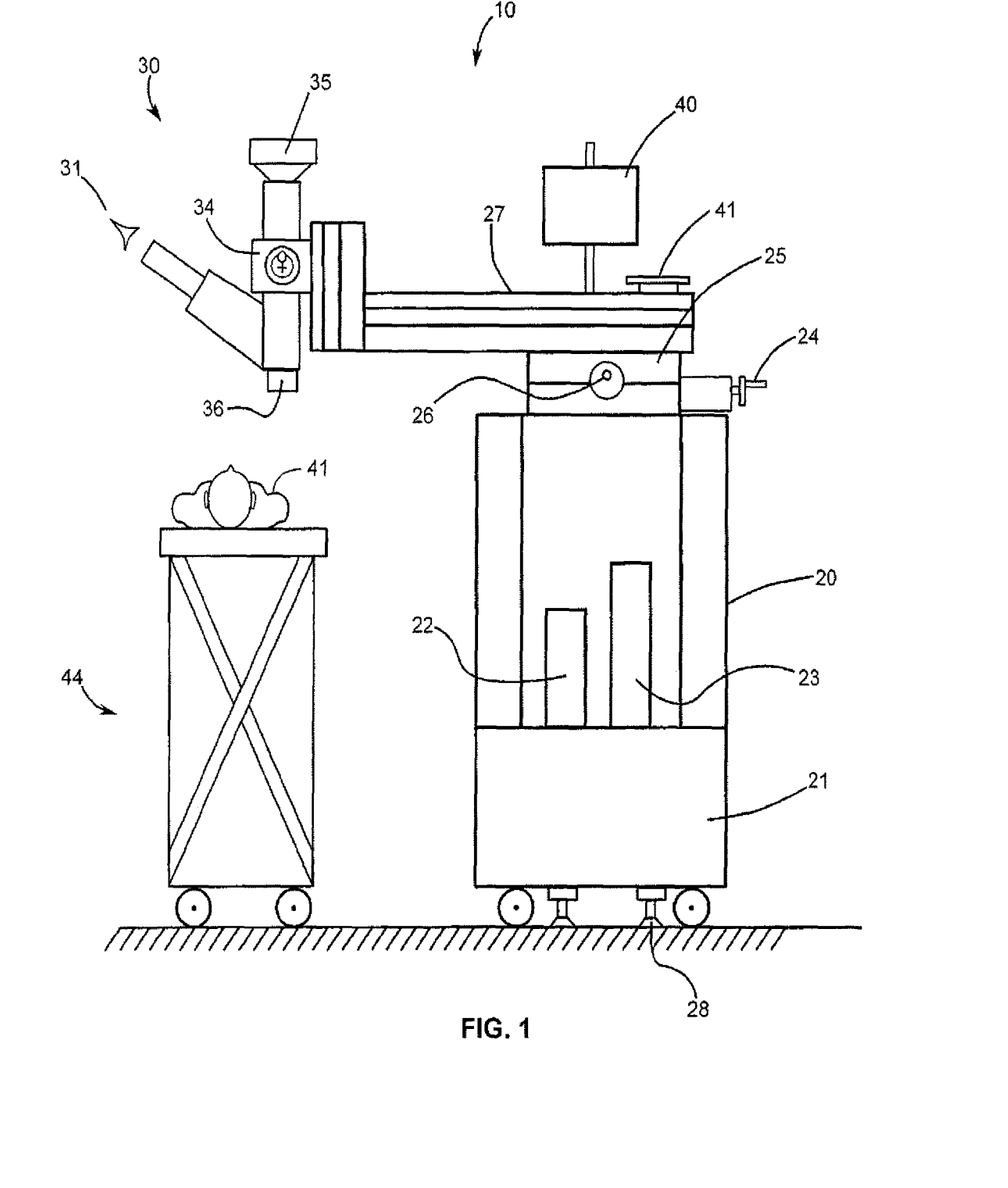
FIG. 1 is an illustration of an embodiment of an improved clinical intravital microscope.

In another aspect of the invention, the microscopic objective 36 will come into close proximity with the tumor tissue for microscopic observation. In one embodiment, fine controls of horizontal and vertical movement 24, 26, 34 are mechanized for ease of use. Once the microscopic objective 36 is in proper position, the epifluorescent light source 22, which is connected to the microscope and camera portion, will be turned on and digital video recording will commence. In another aspect of the invention, video images may be captured to a hard drive in a computer, PDA, CPU or other storage or computing device 23 attached or otherwise connected to the microscope camera 36 (as illustrated in FIG. 1). In addition, data may be backed up on a password-protected hard drive in the laboratory.

Following several observations over various portions of the tumor, fluorescent agents (e.g. 1 ampule (5 mL) 25% fluorescein) may be injected intravenously and observation continues until loss of fluorescence. In one embodiment, IVM is continuously performed at the time the fluorescent agent is injected and video is recorded in real-time. The fluorescence is almost immediately visible within the microscopic field, and the vessels are quickly outlined in great detail. The fluorescence may stay present in the vessels or begin to permeate through the tissue based on the agent being employed. The extravasation of dye may be determined by visualizing fluorescence outside of the defined vessels of the tumor. The distance from the vessels may be measured, recorded, and expressed as a function of time (extravasation rate) in analysis performed off-line from the digitally recorded video. At the completion of the observation period, for example, the microscopic objective 36 may be removed and sterilized between uses. In addition, scope wheels 127 may be unlocked and the scope may be withdrawn.

The observation may take place during the course of standard surgery and is not anticipated to delay or lengthen the duration of the procedure. For example, other portions of the procedure may be continued during the observation period (e.g., preparation and biopsy of the sentinel lymph node if part of the planned procedure). Upon completion of the observation, the wide local excision or tumor extirpation may be completed using "bowel technique." Fresh gown and gloves and fresh, sterile surgical instruments may be used to complete the wide excision or tumor removal to eliminate any chance for tumor seeding in the resection bed.

In one embodiment, the specimen will be removed and undergo standard pathology evaluation. The patient will recover in the post-anesthesia care unit ("PACU") per standard protocol. In addition, off-line analysis of digitally recorded live video may be performed using parameters and statistical methods that have been developed in preclinical imaging studies.

In one aspect, lumenal cross-sectional diameter (D) of vessels and velocity (V) of fluorescein labeled cells may be measured in off-line observations. Wall shear rate may be calculated as 8 (V÷D). Tumor vessel density may be determined by measuring the calculated blood vessel area as a percent of the total visual field area. If visible, the uptake of fluorescent agents into the tumor tissue will be measured as a diffusion rate (distance from tumor vessel over time) and as a percent of the total tumor field observed (percent of visual field expressed as surface area with fluorescein detected). Blood flow velocity may be determined by the equation Q=(RBC velocity/1.6)×(d/2)×pi. In one embodiment, these data are calculated and recorded in a spread sheet that is saved onto a password-protected hard drive.

Referring now to the drawings, and more particularly to FIG. 1, the present invention broadly provides a clinical intravital microscope system, generally indicated at 10. In one embodiment, the system comprises a microscope (microscope eyepiece 31 and objective 36), a heavy base or stand 20, 21, and an arm or cantilever 27 adapted to move horizontally and to extend over the patient. The cantilever arm 27 may be motorized and may have controls 24, 26 for fine control of movement. In one embodiment, the arm 27 rests upon a horizontal positioning table 25 configured to move left and right (horizontally) in the X and Y-axis direction. The table may be mechanized/motorized, or may be manually moveable. Similarly, the microscope and camera portion 30 may be motorized and may have fine controls 34 for vertical movement (in the Z-axis direction) and/or focus. The base 21 may comprise a heavy material such as granite. The camera 35 may be connected to a power source and to a computer 23 via cables or cords. The base 21 may include a stabilizing element 28 near the wheels or incorporated in the wheels.

The novel IVM system may include a monitor 40 and keyboard 41 for input/control of the cantilever 27 and/or control of the light source 22 and/or control of the computer 23. In one embodiment, the light source 22 and computer 23 are positioned within the base 20, 21.

The microscope and camera portion 30 includes a microscopic eyepiece 31, a microscopic objective 36 for positioning over the patient 41, a camera 35, and horizontal and/or vertical motion and/or focus controls 34. The microscope and camera portion 30 is disposed over the patient 41, which patient may be on a cart 44.

Figure 2:
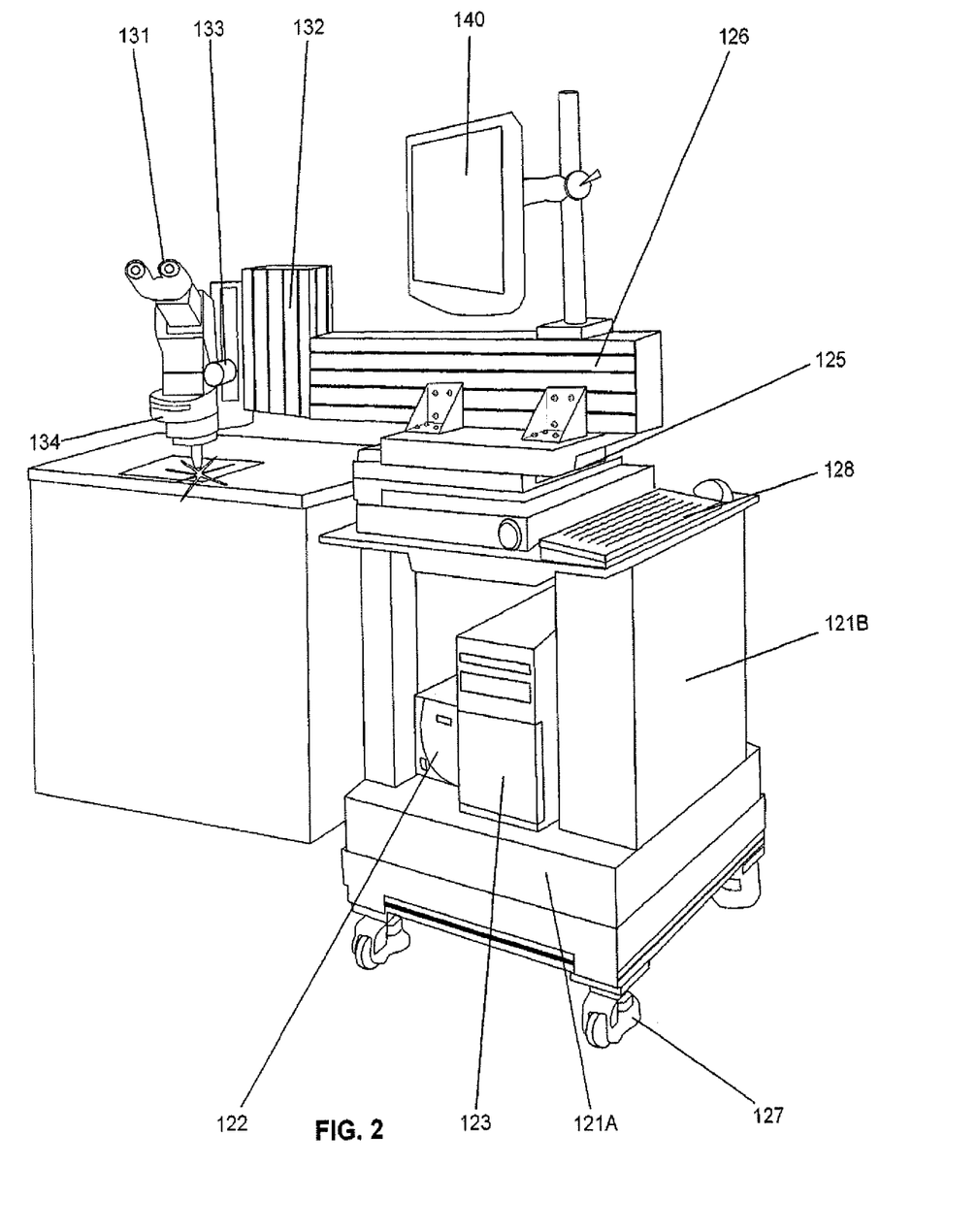
FIG. 2 is a perspective view of an embodiment of an improved clinical intravital microscope.

FIG. 2 is a representation of one embodiment of the present invention. The drawing illustrates a heavy base (such as granite) 121A, 121B with wheels having a stabilizing mechanism 127 (also depicted in FIG. 9). The base also includes, in this example, a light source 122 (such as X-Cite 120 (Lumen Dynamics, Ontario, Canada) or another light source known to those skilled in the art) and a computing device (such as a personal computer) 123. In this embodiment, a keyboard 128 is positioned on the top of the base adjacent to a mechanized position control table 125 for horizontal movement of the cantilever 126. In addition, in this embodiment, a monitor 140 may be used to display output from the camera (135 in FIG. 3), data, or output from imaging software, or other information. Adjustment elements 133 are also disclosed for positioning of the microscope 131, objective and/or camera. The base of a rotating turret 134 is also depicted which permits rotational movement of the microscope.

In one embodiment, the IVM system includes a computer controlled fluorescence microscope such as X-Cite 120 PC Q System with 3 m LLG (this may include an X-Cite 120 PC Q unit with iris (P010-00213); an X-Cite 120 replacement lamp module (P012-63000); and 3 mm×3000 mm LLG (P805-00040)—Microscope Collimating Adapter"). The system may also include a high resolution camera such as an Andor camera or the Luca-R 1004×1002, 8 um, EMCCD, VP, 12.5 MHz, −20C, tri. In addition, software for imaging cameras such as Andor SOLIS for Imaging is used.

The Filter Set may include ET—FITC/Alexa Fluor 488/Fluo3/Oregon Green—Higher throughput, sub-pixel registered, and/or the ET—mCherry, Texas Red (Alexa 568)—Higher throughput, sub-pixel registered.

Figure 3:
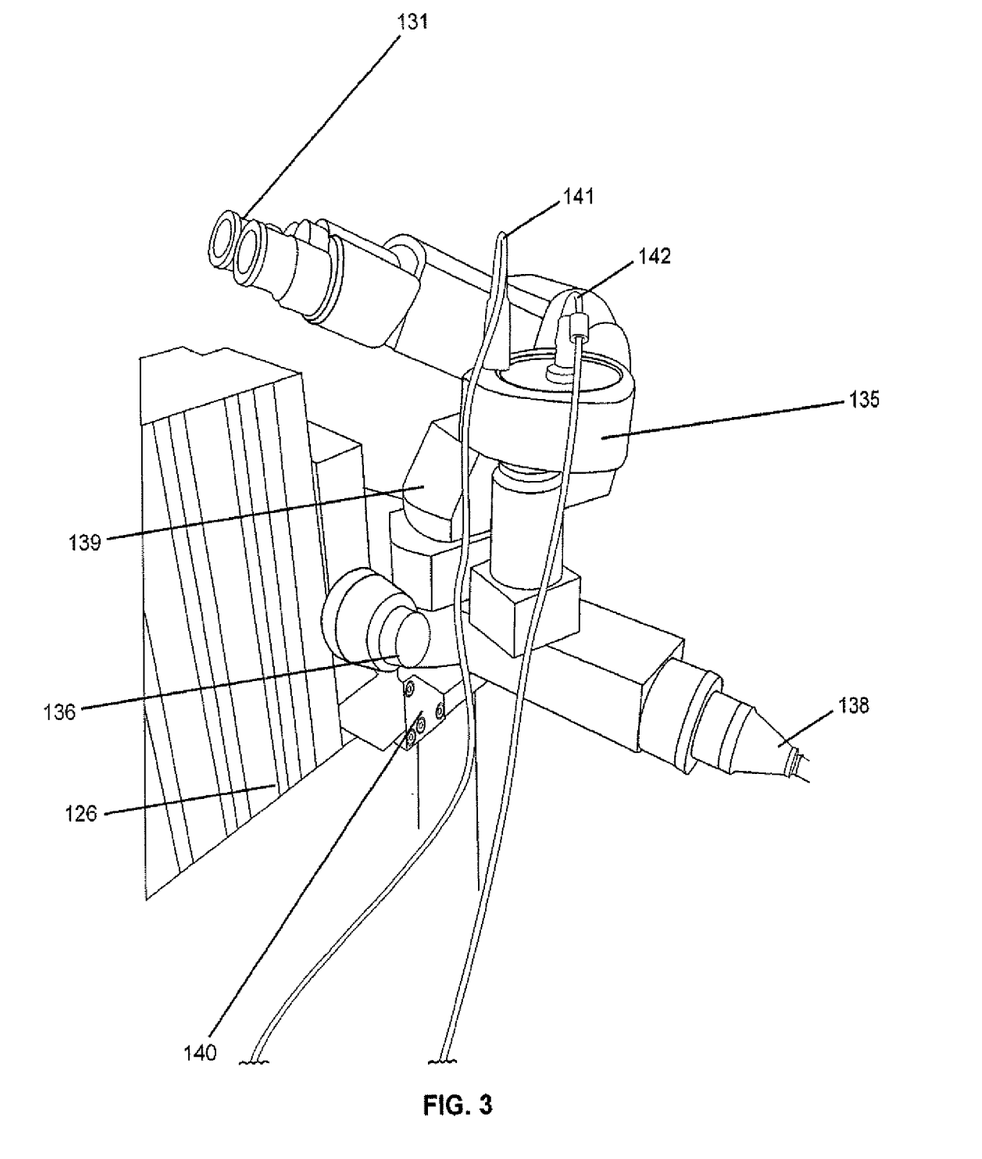
FIG. 3 is a perspective view of the microscope and camera portion of one embodiment of an improved clinical intravital microscope.

FIG. 3 shows the microscope and camera portion of the improved device. FIG. 3 illustrates the microscope eyepiece 131 (which may be, for example, an Olympus eyepiece). In this embodiment the eyepiece portion of the microscope is mounted on a rotating turret 139, and vertical focus controls 136 are included. In addition, an adjustable filter wheel 140 is included. In this example, the camera 135 is made by Andor. FIG. 3 also illustrates the entry point of the fiber optic light source 138, which is connected to light source (122 in FIG. 8) via fiber optic cable, wire or cord.

Figure 4:
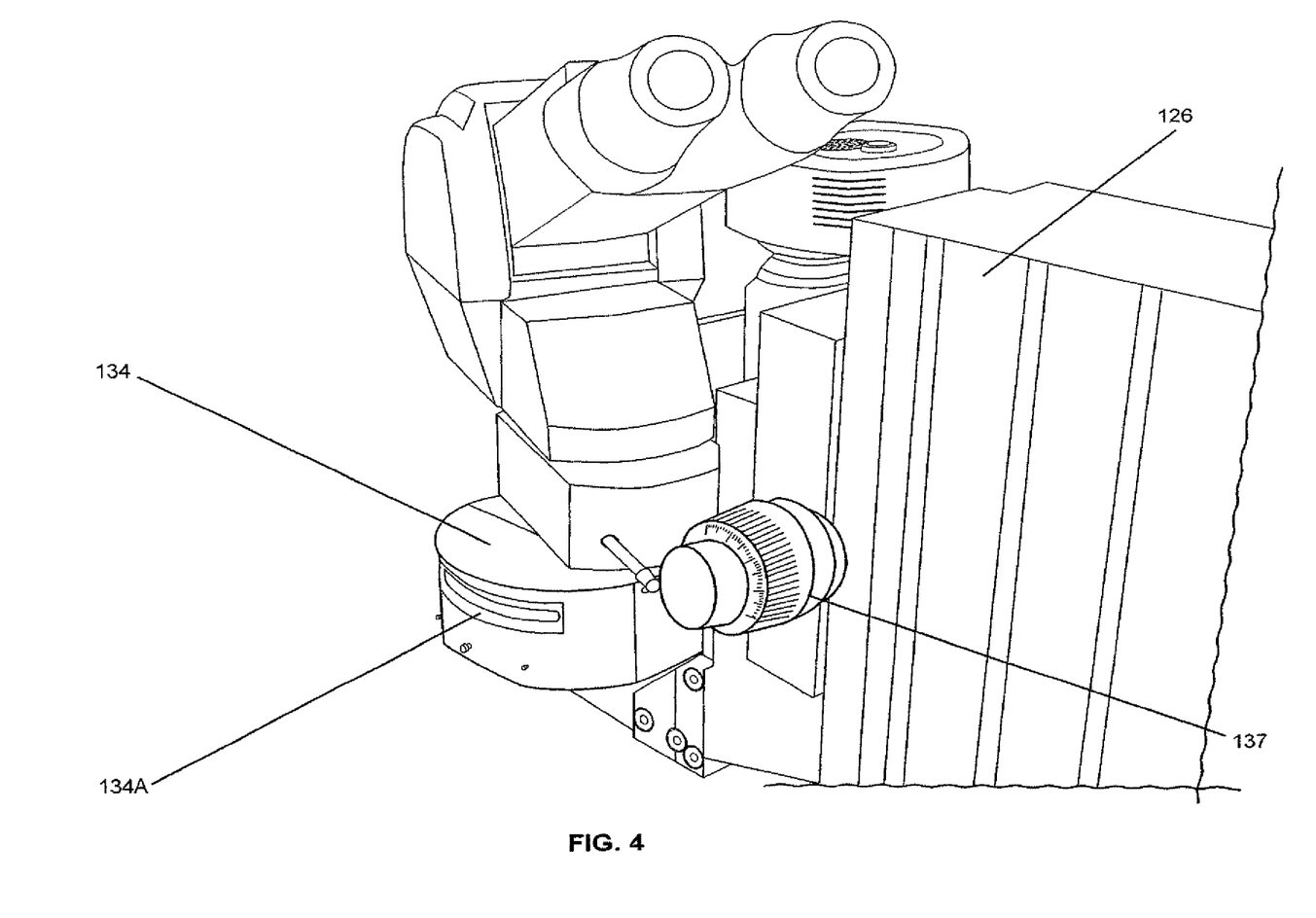
FIG. 4 is another perspective view of the microscope and camera portion.
Figure 5:
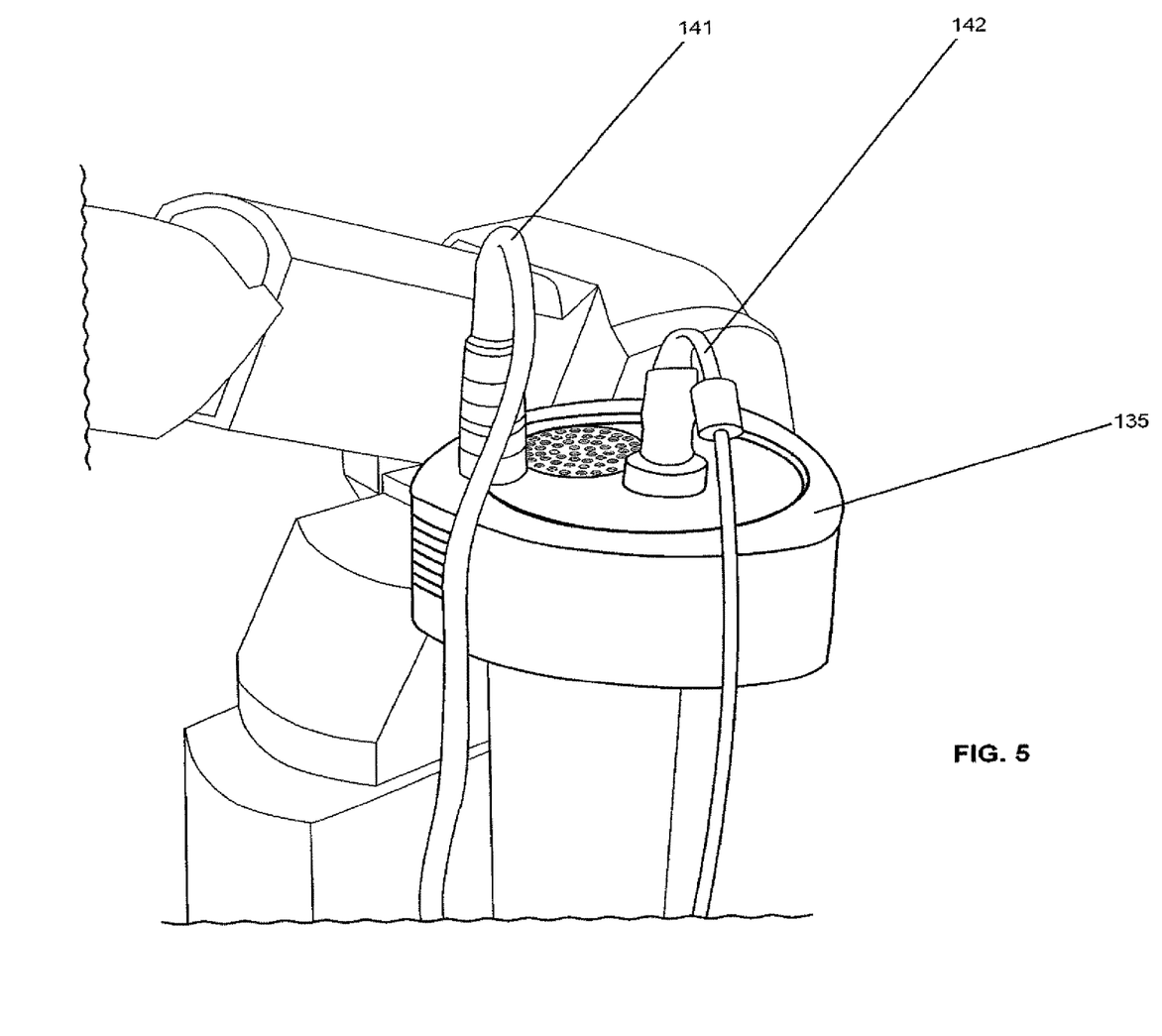
FIG. 5 is a perspective view of the camera portion of on embodiment of an improved clinical intravital microscope illustrating power and computer connections.

FIG. 4 is a perspective view of the microscope and camera portion, which illustrates focus controls 137 and the base of the rotating turret 134, and may include an adjustable wheel filter 134A. FIG. 5 is a detailed view of the camera 135, showing connection to power 141 and output to computer 142.

Figure 6:
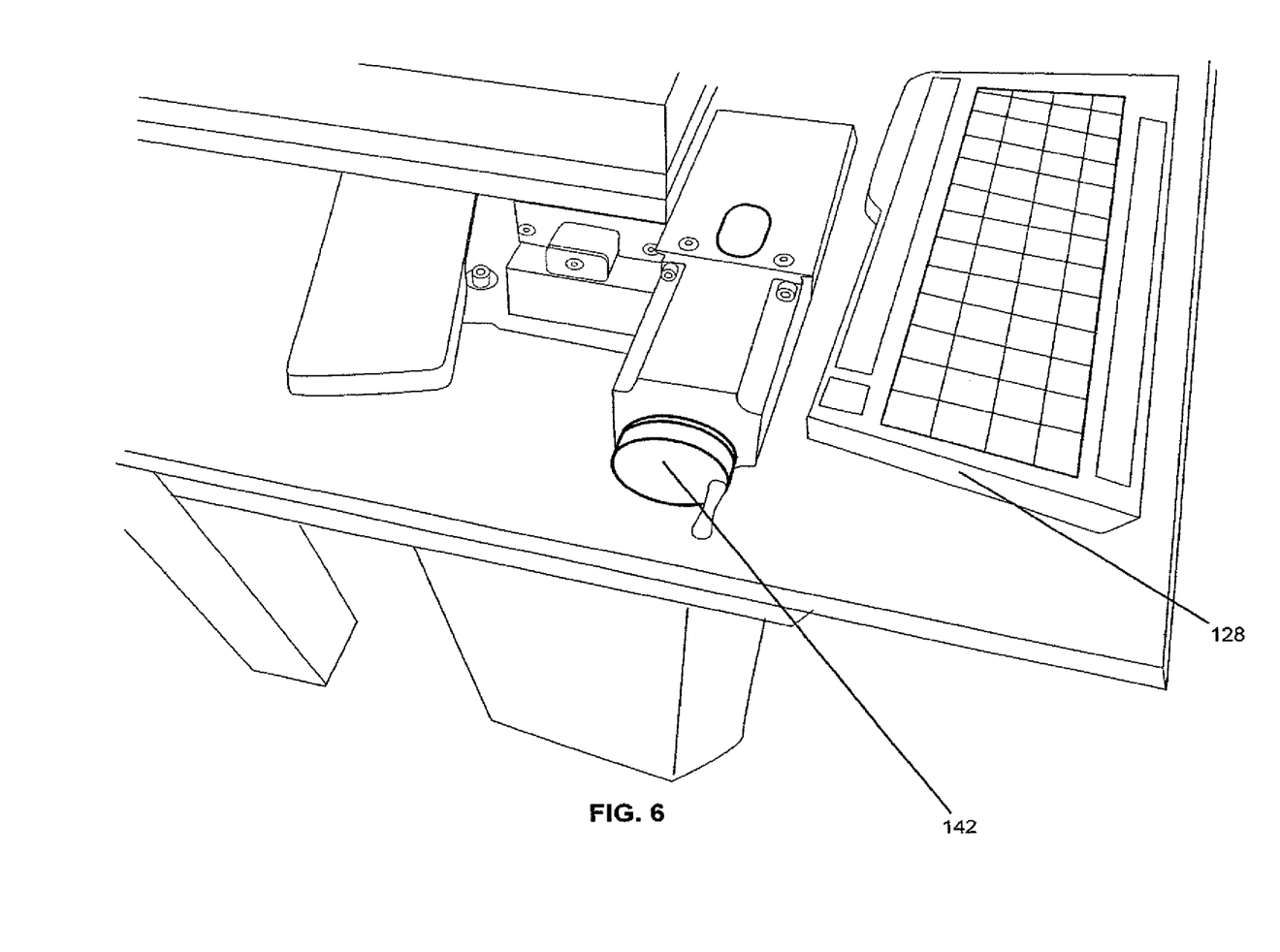
FIG. 6 is a perspective view of the keyboard and horizontal control portion of one embodiment of an improved clinical intravital microscope.
Figure 7:
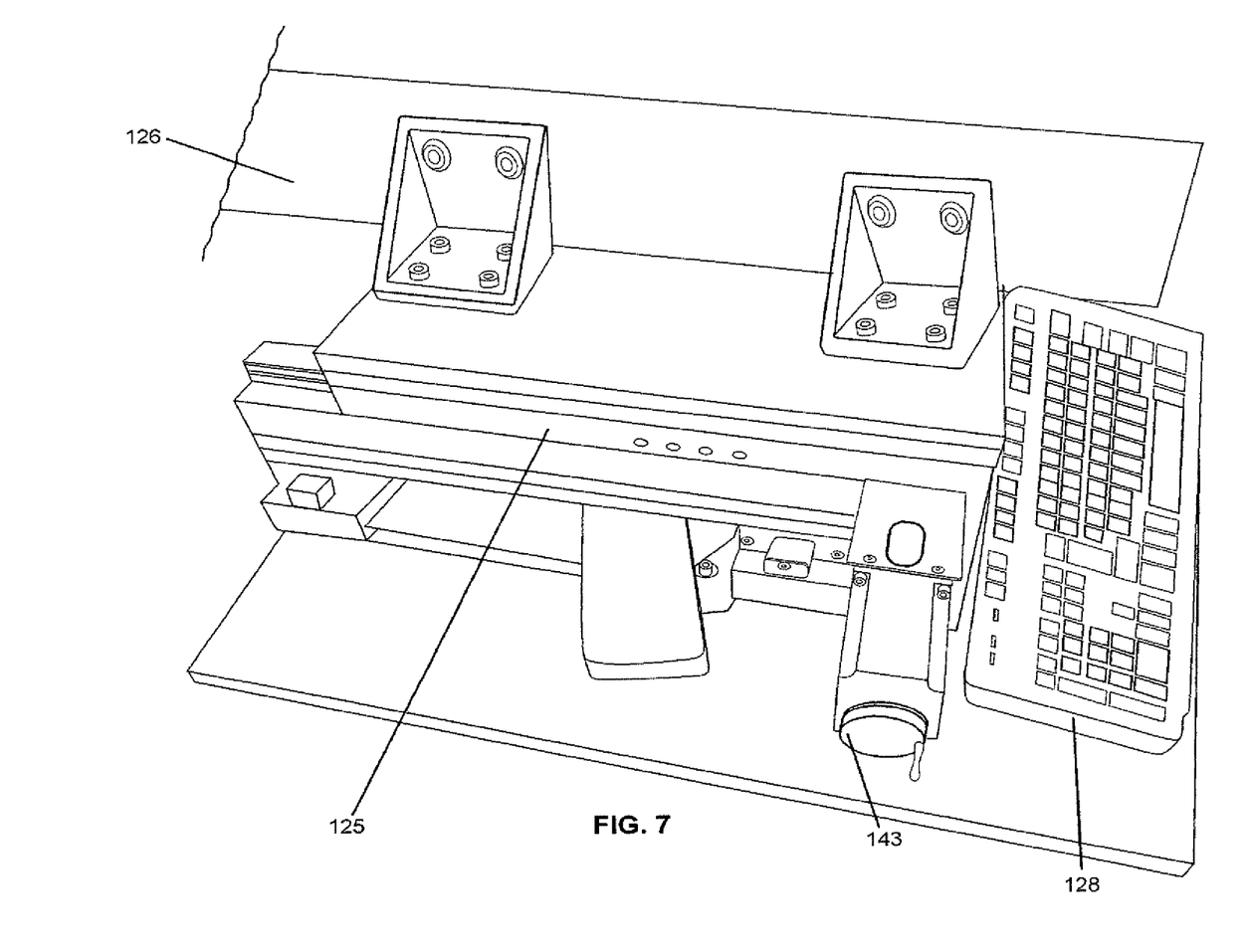
FIG. 7 is a perspective view of the horizontal control portion of an improved clinical intravital microscope.
Figure 8:
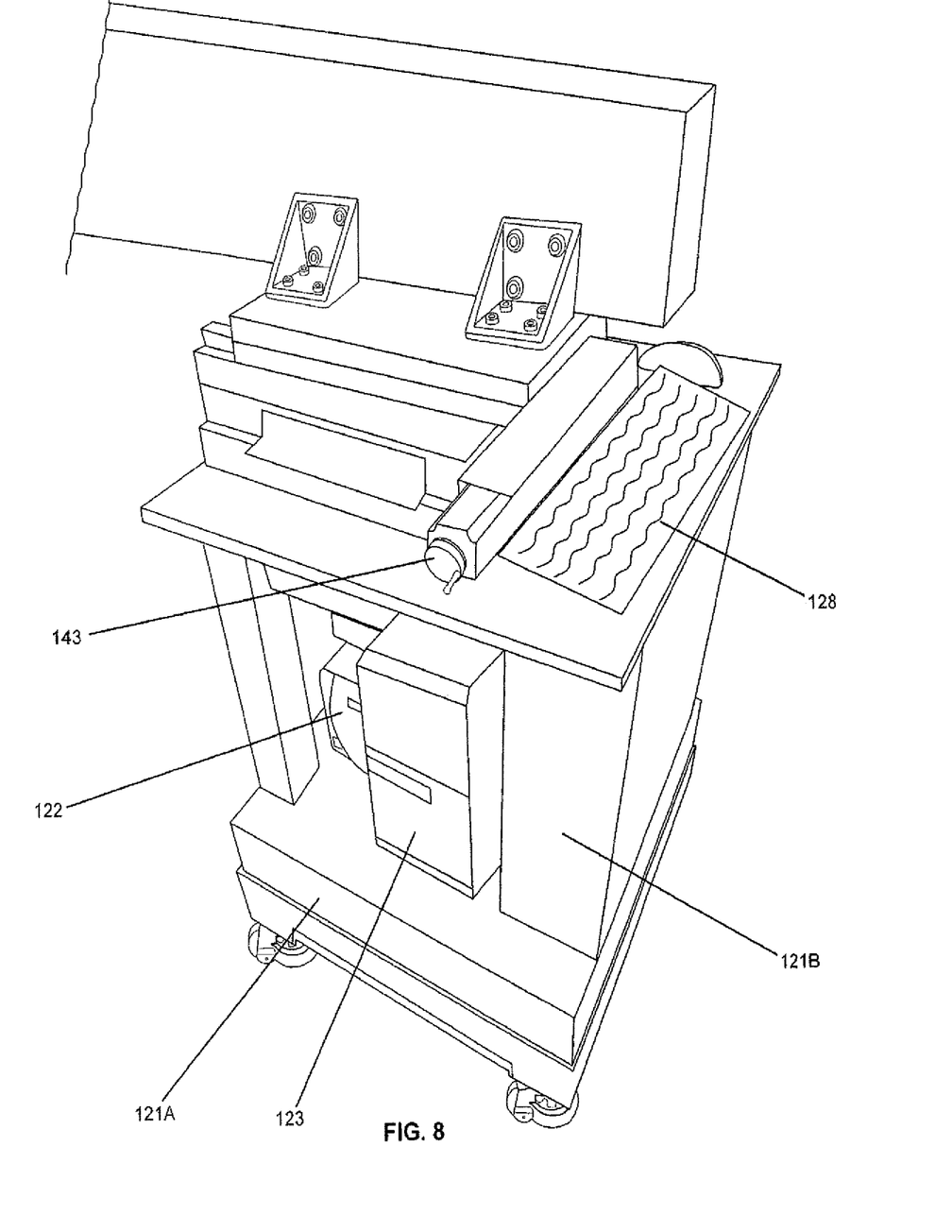
FIG. 8 is a perspective view depicting the base portion of one embodiment of an improved clinical intravital microscope.
Figure 9:
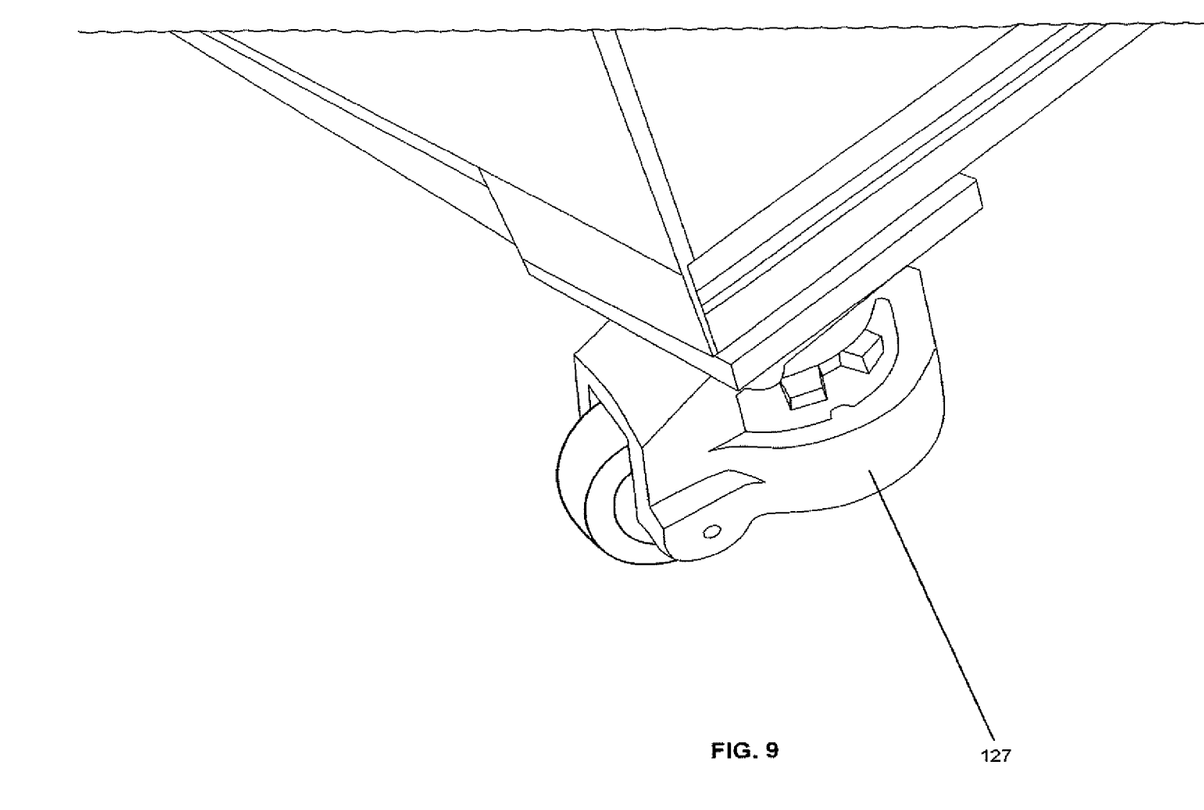
FIG. 9 is a perspective view of a wheel on the base of an improved clinical intravital microscope.

FIG. 6 is a depiction of the keyboard 128 and a portion of the mechanized table for horizontal movement. In this embodiment, a fine control 143 for horizontal movement of the table is illustrated. FIG. 7 is another view of the mechanized horizontal movement table 125, which also shows the cantilever/arm 126 positioned and attached on top of the table. FIG. 8 is an illustration of the base portion depicting heavy granite base members 121A, 121B, and a light source 122 and computer 123 positioned within the base portion. FIG. 9 is a close up of one wheel on the base, which illustrates a stabilizing apparatus 127 to prevent movement of the table.

In one aspect, the intravital microscope system is constructed in a cantilever configuration with an arm 27 that extends over the patient and is stabilized by ~800 lbs. (or similar weight) of a granite base. The cantilever may be adjustable and portions may be motorized for fine control of movement (x+y) directions with a manual control over focus (z). The incorporation of the granite base 20, 21 and software to minimize motion artifact make human intravital microscopy possible and is significantly different than prior animal applications in the laboratory.

There are many advantages and improvements of the novel clinical IVM. In one aspect, the microscope may be configured to allow for the visualization of human tumors in situ at a magnification of 100×, in real-time and generate dynamic data that has never been collected clinically. There are no current methods to obtain microscopic visualization of dynamic processes at this level of magnification in humans. The use of this microscope can allow for the live characterization of human tumors to predict outcomes, direct subsequent therapies, and determine host-tumor interactions in vivo to improve outcomes.

Several major obstacles were overcome during the design and implementation of this technology to allow for the first human intravital microscopic observation. The novel intravital microscope is fully functional and can obtain dynamic data. The use of the human intravital microscope is anticipated to revolutionize the way cancer treatment decisions and prognostic information is obtained.

EXAMPLE

Patient Selection

Patients with a visible (>0.5 cm in maximal diameter) or palpable melanoma lesion that required excision in the operating room were evaluated. Eligible patients were enrolled in the protocol and information was recorded including demographic data (age, gender, height, and weight), tumor-specific data (tumor type, location, depth from skin, and stage) as well as photographs from the surgery. Although the reported risk of anaphylactic reaction to fluorescein is low (1 in 222,000), a skin-prick test was performed on all enrolled patients to determine potential sensitivity. At least 24 hours prior to surgery and the planned microscopic observation, the volar aspect of the patient's non-dominant forearm or opposite side of disease was prepped with an alcohol pad. Three separate areas were demarcated for testing with a marking pen and solutions consisting of 10 microliters of 10% fluorescein, histamine chloride (10 mg/ml) [positive control], and 50% saline solution [negative control] were placed appropriately. The skin underlying each solution was individually pricked with separate and sterile Duotip® lancets (Lincoln Medical, USA). After 30 minutes, the appearance of a wheal greater than 3 mm in diameter was considered a positive test result in the context of the appropriate positive and negative control. If a positive test was noted to fluorescein, the patient was excluded from the study.

Surgical Technique

Prior to definitive surgical excision, melanoma tumors were exposed in a consistent manner. The skin overlying the tumor was prepped with ChloraPrep (CareFusion Corp. San Diego, Calif.) and sterile towels were applied for exposure of the area. A curvilinear incision within the field of planned resection was created with a scalpel in line with the longitudinal axis of the patient. With care to keep the vasculature intact, the skin was elevated bluntly and retracted laterally with the use of 0 silk sutures. Electrocautery was avoided as much as possible to prevent underlying tissue damage. The sutures were anchored to a retractor affixed to the operating room ("OR") table on the opposite side of the planned microscopic observation. For deeper melanoma tumors, a self-retaining Weitlaner retractor was used following incision of the skin and underlying subcutaneous tissue. In all instances, a saline-soaked gauze was placed over top of the tissue to prevent desiccation prior to microscopic interface. After exposure of the underlying tumor mass, the microscope was positioned for observation. At the completion of the observation period, the microscope was withdrawn and the skin flap was closed with a running 3-0 silk suture. The area was then re-prepped for the definitive oncologic surgery including a new skin prep, sterile towels and drapes, and new gown and gloves.

Microscope Design and Observation

Patient tumors were observed at 100× magnification using a customized Olympus microscopy system (Spectra Services, Rochester, N.Y.). The microscope was attached to a cantilevered arm to extend over the patient. Given the high magnification required to observe individual vessels and flow, vibrations in the microscope were dampened using a weighted marble base of over 360 kg. Fluorescein was illuminated using a 467-498 nm excitation 513-556 emission dichroic filter set (Spectra Services, Rochester, N.Y.) with an X-Cite 120 Led light source (Lumen Dynamics, Ontario, Canada). Images were captured using a Luca EMCCD camera (Andor Technology Ltd., Belfast, Northern Ireland) controlled through the Solis acquisition and analysis program. Images were acquired with a minimum of a 0.05 s exposure at 20 frames a second. The microscope was grossly moved into position by the surgeon over the field of interest and locked into place. Fine adjustments in the x and y axis were performed by using the built-in motor controls. Once the microscope was directly overlying the exposed tumor tissue, the fluorescent light source and image acquisition software were activated. Vertical control of the microscope was performed manually by the surgeon until tumor vessels came into view on the digital monitor. Tumor vessels were clearly recognized by their atypical architecture, coiling, and branching patterns and observations focused on these areas. To facilitate stabilization of the images, respirations were temporarily held by anesthesia for a maximum of 30 seconds. When a stable view of the vessels was achieved, 0.5 ml of 25% (250 mg/ml) fluorescein (Akorn Inc., Lake Forest, Ill.) was injected via a peripheral intravenous catheter. An observation was completed when fluorescein was noted to have extravasated into the tumor tissue and the vessels no longer manifested a detectable fluorescent signal. The microscope was then re-positioned with fine motor controls to observe a different tumor area. The microscopic observations were finalized when the 2 ml of fluorescein was exhausted.

Post Hoc Analyses

Offline quantification of vessel diameter and blood velocity was performed using the Image software suite. Vessels were defined morphologically and a single vessel was described as beginning at a branch point continuing to the next branch point. To be measured, vessels had to be 100 μm in length with no branch points. Vessel density was established by enumerating vessels within a field of observation. Image software was used to measure vessel diameter at the vessel's largest width. Blood flow rate was evaluated by determining the time ΔT distinct features in the fluorescent dye would take to travel a known distance ΔS and then averaging ΔS/ΔT for at least 10 points per vessel.

Murine IVM

106 B16/F10-OVA melanoma cells, established from mycoplasma-free frozen stocks, were injected subcutaneously in the flank of 8-10 week-old Female C57BL/6 mice (National Cancer Institute). Experimental analysis was performed 2-3 weeks post-implantation. Mice were anesthetized with Ketamine/Xylazine (100 mg/10 mg per kg) injected into the peritoneum. The skin overlying the tumor was incised and retracted with care to keep the vasculature intact in a manner identical to the human melanoma tumors. Vessels were visualized and video recorded by the same epifluorescent intravital microscope platform used in humans. Lumenal cross-sectional diameter (D) of vessels was measured in off-line observations of five mice.

Tissue Processing

Histologic sections were stained with standard Hematoxylin and Eosin (H&E) and for CD31 (Human—1:50 dilution, Clone JC70A, Dako, Carpinteria, Calif., Murine—1:20 dilution, Clone SZ31, Dianova, Hamburg, Germany). Stained sections were scanned with an Aperio Scanscope XT (Leica Microsystems Inc., Buffalo Grove, Ill.) and evaluated using Aperio Spectrum software. Vessel density was assessed using standard "hot spot" methodology. For each tumor, vessels in five separate hot spot fields were counted at 200× total magnification. In these same fields, the maximum cross sectional diameter was measured in all vessels with an identifiable lumen. Measurement utilized the Spectrum software toolset.

Statistical Analyses

Unpaired Student t-tests were utilized to examine differences between vessel diameters measured by human IVM, IHC, and murine IVM, IHC. Unpaired Student t-tests were utilized to examine differences between blood flow rates measured by human IVM. No statistical method was used to predetermine sample size.

CONCLUSION

Through use of the method of one embodiment of the invention, valuable data was obtained regarding vascular parameters that could not have been predicted by IHC or preclinical mouse studies. The calculated diameters measured in the tumor-associated vessels by IHC in the same tumor tissue were significantly smaller than those measured by real-time live imaging microscopy. This finding can be partially attributed to the "shrinkage" of tissue that typically occurs with formalin-fixation which was an approximate 62% reduction from IVM-measured vessel diameters in the study. More importantly, the luminal diameter seen by IVM is likely larger due to the natural distention of vessels in living tissue as a result of mean arterial pressure. Since there was good uniformity in IHC tumor vessel diameter measurements throughout patient melanoma tumors, it is unlikely that disparities in tumor vessel diameters were related to a limited sampling of the superficial tumor vessels measured by IVM. The tumor vessel diameters measured by IVM in a preclinical mouse model of melanoma using the same methodology and microscope also underestimated the diameters seen in human melanoma tumors. These results further support the concept that shrinkage that occurs during formalin fixation is not the sole cause of differences in vessel diameter measurement detected by IVM and IHC in human tumors. The smaller diameters of tumor vessels detected by IVM in preclinical models may be species-specific and potentially related to the nature of rapidly growing, implantable tumors that differ from the protracted growth trajectory of orthotopic tumors found in humans. However, unlike human tumors, the murine model did not demonstrate any significant difference in tumor vessel diameters when measured by IVM versus IHC.

The importance of these findings is profound when considering that diameter is a component of calculations used to predict tumor tissue perfusion and drug delivery, and to date, assumptions of diameter could solely be based on IHC and preclinical IVM. For example, a recent review on strategies for tumor vessel normalization to improve drug delivery and perfusion assumed a standard tumor vessel diameter of 15 μm based on available data from preclinical models, which is in direct line with the observed IHC and murine IVM diameters, but substantially undervalues the consistently larger diameters measured by human IVM (average 33 μm) in the current study. The discrepancy in diameter measurements is magnified when considering the relationship of vessel wall shear stress which is inversely proportional to the radius cubed, so that even minor changes in calculated diameters may have dramatic impact on shear stress calculations. Therefore, the novel view provided by IVM of human tumors prior to resection offers a more accurate assessment of tumor vessel characteristics that may be leveraged to influence therapeutic considerations.

The observation of non-functional tumor vessels, which has been reported in preclinical models, was readily evident. Importantly, non-functional vessels were noted in transcutaneous IVM observations which excluded the potential for artifact associated with surgical exposure. Since single-photon IVM is limited by the depth of epifluorescent light penetration (i.e. 70 μm), it cannot be determined whether diameter, blood flow rates, or the percentage of functional vessels vary within deeper tumor regions. It has been well established that tumor vasculature is heterogeneous, thus an attempt was made to interrogate as many possible areas of the exposed tumor to generate a broad view that was representative of the entire lesion. As the IVM measurements were fairly consistent both within individual tumors and between patients, this would suggest an adequate sampling of tumor fields and measurement accuracy. Despite a limited view of deeper tumor regions, the collection of data regarding the tumor vascular blood flow and architecture from superficial vessels may offer clinically relevant prognostic information as has been previously described in animal models and preliminary human studies using magnetic resonance imaging and complex mathematical estimations of tumor vascularity. For example, the detection of microvascular loops and networks by standard IHC in ocular melanoma vessels has been directly correlated to decreased survival. It is possible that IVM of human tumors may reveal vessel patterns and characteristics that may be linked to tumor aggressiveness and patient prognosis. Studies according to the method of the present embodiment with larger numbers of patients and various tumor types will be able to correlate clinical outcomes and tumor vascular parameters identified by live imaging.

IHC has been responsible for major advancements in tumor biology and represents the clinical standard; however, functional assessment of tumor vessels by IHC is limited. For example, microscopic evaluation of IHC-stained tumor sections represents a single moment in time and cannot determine the patency or blood flow of discrete tumor vessels. While the perfusion of tumor tissue can be inferred by the injection of contrast agents that are measured by IHC after the tumor is removed, this method lacks the ability to follow changes over time in a growing tumor. Interestingly, the IVM platform combined with the choice of fluorescein, visualized the immediate extravasation of fluorescent signal into the tumor tissue. Fluorescein with a molecular weight of 332 g/mol is in the size range of commonly used chemotherapeutic agents (e.g. 5-FU [130 g/mol], cyclophosphamide [261 g/mol], and oxaliplatin [397 g/mol]). The immediate extravasation of fluorescein indicates that this live imaging platform can be used to evaluate the nature of drug distribution within tumors in real-time. Ultimately, dynamic data acquired by IVM may augment data generated from IHC of human tumors, and these techniques may become complementary to provide a more clinically accurate assessment of tumor vasculature.

Despite the multiple obstacles to IVM associated with human melanoma tumors, this technology successfully measured vascular parameters in the majority of cases. Melanoma tumors were chosen as a stringent model for human IVM as they are typically superficial in the dermal or subcutaneous tissue. An advantage of selecting melanoma tumors was their associated dense pigmentation which allowed for confirmation of microscopic localization within bona fide tumor tissue. Contrarily, the significant pigmentation did limit the amount of information that could be collected regarding the tumor-associated blood vessels prior to fluorescein injection. The exposure of the melanoma tumors required a delicate skin flap technique that would be unnecessary for tumors within the peritoneal or pleural cavities. Thus, clinical IVM to observe vascular function may be even more applicable to a wide range of human primary and metastatic tumors as compared to melanoma.

The potential applications of this technology are abundant in the field of clinical oncology. The observation of tumor features beyond simple vascular measurements is likely possible, including the ability to determine the physiologic state of the tumor in regards to pH, hypoxia, and metabolism which have been evaluated successfully using IVM in preclinical rodent models. Responses to therapies targeting the tumor vasculature may be observed over time with this technology. Also, as certain chemotherapy agents are known to be auto-fluorescent, drug uptake and distribution studies are now possible in real-time. The human IVM platform may allow for the design of fluorescent substrates that can signal the presence of particular mutations or other tumor targets to guide therapy at the time of tumor removal. Additionally, human IVM will have direct application to assess the delivery of fluorescently-tagged cytotoxic T cells to tumor beds during adoptive transfer cancer immunotherapy and shape future clinical trials. In this regard, it remains to be determined whether poor rates of T cell trafficking in human tumors is a mechanism of immune evasion as we have reported for murine tumors. In summary, the novel application of IVM in humans has been demonstrated to be feasible and phenomena were observed that could not have been anticipated by currently available state-of-the-art methodologies. It is anticipated that these findings will serve as a launching point for a wide array of clinical investigations in the field of oncology.

Intravital microscopic imaging during the surgical removal of human melanoma tumors revealed that approximately half of human tumor vessels do not support blood flow and have greater diameters than could be predicted by existing methodologies such as conventional immunohistochemical analysis of patient tumors or from preclinical murine models.

The present invention contemplates that many changes and modifications may be made. Therefore, while the presently-preferred form of the clinical intravital microscope has been shown and described, and several modifications and alternatives discussed, persons skilled in this art will readily appreciate that various additional changes and modifications may be made without departing from the spirit of the invention, as defined and differentiated by the following claims.

What is claimed is:

1. An intravital microscope system for observing tissues of a human patient in real-time during a medical procedure, the system comprising:
   a heavy base having one or more wheels for moving the base on a support surface;
   an arm having a proximal and a distal end, the proximal end of the arm supported by the base, the arm extending horizontally from the base;
   an intravital microscope having an eyepiece and an objective, the intravital microscope mounted on the arm, wherein the intravital microscope has a magnification between about 100× and 200×;
   a video camera operatively associated with the intravital microscope;
   a surface for supporting the human patient underneath the intravital microscope;
   a processor for receiving and storing video images from the camera and for minimizing motion artifact; and,
   wherein the base and the processor for minimizing motion artifact are configured and arranged to provide visualization of tumors in situ in the human patient in real time to generate dynamic data.

2. The system of claim 1, wherein the microscope is configured and arranged for adjustment in an X and Y-axis.

3. The system of claim 1, wherein the microscope is configured and arranged for vertical adjustment in a Z-axis.

4. The system of claim 1, wherein the base further comprises a stabilizing element.

5. The system of claim 1, wherein the patient supporting surface is disposed on a cart having a plurality of casters disposed thereon.

6. The system of claim 1, further comprising a fluorescent illumination source.

7. The system of claim 6, wherein the illumination source is epifluorescent.

8. The system of claim 1, wherein the microscope is configured and arranged to be adjusted in a Z-axis relative to the arm.

9. The system of claim 1, wherein a position of the arm is adjusted by a motorized system.

10. The system of claim 1, wherein the arm is a cantilever.

11. The system of claim 1, wherein the processor is disposed inside the base.

12. The system of claim 6, wherein the illumination source is disposed inside the base.

13. The system of claim 1, wherein the intravital microscope is mounted on a rotating turret.

14. A method for observing tissues of a human patient, the method comprising:
   providing a heavy base having one or more wheels for moving the base on a support surface;
   providing a stabilized arm such that motion artifact in the system is minimized;
   providing an intravital microscope having an eyepiece and an objective, the intravital microscope mounted on the arm, the intravital microscope has a magnification between about 100× and 200×;
   providing a video camera operatively associated with the intravital microscope;
   providing a surface for supporting the human patient underneath the intravital microscope; and, using the intravital microscope to observe the tissues in real-time.

15. The method of claim 14, further comprising providing visualization of human tumors in situ in real-time.

16. The method of claim 15, further comprising observing and/or recording conditions selected from the group consisting of blood flow, vessel density, tumor structure, tumor size and tumor shape.

17. The method of claim 14, further comprising a processor provided with software for minimizing motion artifact.

* * * * *